(12) United States Patent
Bitter et al.

(10) Patent No.: US 6,259,763 B1
(45) Date of Patent: Jul. 10, 2001

(54) X-RAY IMAGING CRYSTAL SPECTROMETER FOR EXTENDED X-RAY SOURCES

(75) Inventors: Manfred L. Bitter, Princeton, NJ (US); Ben Fraenkel, Jerusalem (IL); James L. Gorman, Bordentown, NJ (US); Kenneth W. Hill, Lawrenceville, NJ (US); A. Lane Roquemore, Cranbury, NJ (US); Wolfgang Stodiek, Princeton, NJ (US); Schweickhard E. von Goeler, Princeton, NJ (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 09/315,834

(22) Filed: May 21, 1999

(51) Int. Cl.[7] ............................................. G01T 1/36
(52) U.S. Cl. ................................... 378/82; 378/84
(58) Field of Search .................... 378/82, 84, 71, 378/72, 83, 49; 250/51.5, 49.5, 445

(56) References Cited

U.S. PATENT DOCUMENTS

| | | | |
|---|---|---|---|
| 2,557,662 | * 6/1951 | Kirpatrick | 250/53 |
| 3,079,501 | * 2/1963 | Birks, Jr. | 250/51.5 |
| 3,439,163 | * 4/1969 | De Jongh | 250/51.5 |
| 3,983,398 | * 9/1976 | Boyd | 250/445 |
| 4,426,719 | * 1/1984 | Fraenkel | 378/70 |
| 4,553,253 | * 11/1985 | Petersen | 378/84 |
| 4,807,268 | * 2/1989 | Wittry | 378/84 |
| 4,949,367 | * 8/1990 | Huizing et al. | 378/84 |
| 5,887,048 | * 3/1999 | Sata et al. | |

FOREIGN PATENT DOCUMENTS 6-258497 * 9/1994 (JP) ....................................... 378/84

OTHER PUBLICATIONS

G. Tondello, Optica Acta, 1979, vol. 26, No. 3, 357–371.*

* cited by examiner

Primary Examiner—Robert H. Kim
Assistant Examiner—Irakli Kiknadze
(74) Attorney, Agent, or Firm—Joy Alwan; Thomas G. Anderson; Virginia B. Caress

(57) ABSTRACT

Spherically or toroidally curved, double focusing crystals are used in a spectrometer for X-ray diagnostics of an extended X-ray source such as a hot plasma produced in a tokomak fusion experiment to provide spatially and temporally resolved data on plasma parameters using the imaging properties for Bragg angles near 45. For a Bragg angle of 45°, the spherical crystal focuses a bundle of near parallel X-rays (the cross section of which is determined by the cross section of the crystal) from the plasma to a point on a detector, with parallel rays inclined to the main plain of diffraction focused to different points on the detector. Thus, it is possible to radially image the plasma X-ray emission in different wavelengths simultaneously with a single crystal.

15 Claims, 4 Drawing Sheets

X-RAY IMAGING CRYSTAL SPECTROMETER FOR EXTENDED X-RAY SOURCES

CONTRACTUAL ORIGIN OF THE INVENTION

The United States Government has rights in this invention pursuant to Contract No. DE-AC02-76-CH03073 between the U.S. Department of Energy and Princeton University.

FIELD OF THE INVENTION

This invention relates generally to diagnostic apparatus for use with an extended X-ray source and is particularly directed to a doubly focusing crystal spectrometer for providing spatially and temporally resolved diagnostic data on hot plasmas. In addition to these diagnostic applications for the investigation of extended plasma sources, the doubly focusing crystal spectrometer can also be used to generate radiation fields with a large cross-section of parallel, or near parallel, monochromatic X-rays. Such radiation fields are of interest for the spectral analysis of the composition of an object or body under study—for example, for the detection of forgery in a painting—and may find applications in other areas such as medicine and lithography.

BACKGROUND OF THE INVENTION

X-ray crystal spectroscopy has played an important role in the diagnostics of tokamak fusion plasma, in particular, by Doppler measurements of the central ion temperature, which was, in general, determined from the Doppler width of the resonance lines of the helium-like ions of medium-Z elements, like Ar, Ti, Cr, Fe and Ni. The observed satellite spectra of these heliumlike ions also provided information on various other plasma parameters, e.g., central electron temperature, ionization balance and ion impurity transport.

X-ray crystal spectroscopy is expected to become even more important for the diagnostics of future large hot plasmas, such as will be produced in the International Thermonuclear Experimental Reactor (ITER), because other diagnostic methods will encounter technical difficulties and not be able to measure the central plasma parameters of this fusion device. X-ray lines from high-Z elements such as krypton in the He-like charge state will be well-suited for measurement of the central ion temperature and other central plasma parameters at ITER.

However, the requirements for X-ray crystal spectrometers will change as experimental fusion plasmas increase in size and approach break-even conditions. Under these conditions, the plasma will emit neutrons and gamma radiation. It will therefore be necessary to restrict the size of diagnostic windows and to place diagnostic instruments at large distances from the plasma. Moreover, the concentration of high-Z impurities in the hot core of the plasma will have to be as small as possible, in order to avoid an unacceptable dilution of the burning hydrogen plasma. This latter requirement, especially the intensity of the X-ray line radiation which is needed for plasma diagnostics, will be severely reduced. For the X-ray diagnostics of the core plasmas in future large fusion devices, such as ITER, it is therefore necessary to develop new types of crystal spectrometers having improved focusing properties and which employ very large crystals to enhance the spectrometer throughput or the X-ray flux to the detector.

Crystal spectrometers with improved focusing properties are also needed for the diagnostics of present-day tokamak and stellarator plasmas to satisfy the demands for advanced diagnostics having good spatial resolution and which are capable of providing an image of an extended plasma. The requirements that apply to an imaging X-ray crystal spectrometer for the present-day plasma devices are, however, distinctly different from the requirements for future large devices, such as ITER, which are discussed above. The experimental constraints at present devices are less restrictive because the background of neutron and gamma radiation is orders of magnitude smaller than expected in ITER. The diagnostic windows are larger and the diagnostic instruments are closer to the plasma than they will be in ITER. It is therefore possible to view a large part of present plasmas and to obtain information on the spatial distribution of plasma parameters.

The presently used instruments are Johann spectrometers with cylindrically bent crystals. These instruments only provide focusing for the meridional rays, which are parallel to the main diffraction plane, whereas the sagittal rays, which are oblique to the plasma, are not focused. With exception of the experimental arrangement by Bartiromo et al. (see discussion below), information on the spatial distribution of plasma parameters was previously obtained by arrays of such Johann spectrometers, where each spectrometers records spectra from a single line of sight through the plasma. The number of spectrometers and thus the number of lines of sight, which can be installed at a tokamak is limited and usually not larger than five, because of experimental and budget constraints. The experimental arrangement by Bartiromo et al. also uses a Johann spectrometer with a cylindrically bent crystal. However, in Bartiromo's arrangement, there is a horizontal slit between the crystal and the plasma, so that rays, which emanate from different parts of the plasma above or below the main diffraction plain pass through the slit and are reflected from different parts of the crystal below or above the main diffraction plain onto the detector. Although this arrangement provides spatial resolution in the plasma, the throughput of the instrument is significantly reduced by the slit.

The present invention addresses the limitations of the prior art in terms of future more demanding applications by providing a doubly focusing crystal spectrometer capable of providing simultaneous measurements of spectra from an essentially unlimited number of lines of sight (or chords) through the plasma and thus produce an image of the plasma in a direction perpendicular to the main diffraction plane.

OBJECTS AND SUMMARY OF THE INVENTION

Accordingly, it is an object of the present invention to provide an X-ray spectrometer employing a single crystal for the spatial and temporal resolution of the parameters of an extended hot plasma.

It is another object of the present invention to permit the observation and study of an extended hot plasma simultaneously from many different lines of sight through the plasma.

Yet another object of the present invention is to provide an X-ray spectrometer employing a very large, single, spherically or toroidially curved crystal for improved spectral analysis of the composition of an object under study.

A still further object of the present invention is to provide the monochromatic radial imaging of the X-ray emission of an extended hot plasma for studying the transport and confinement characteristics of the plasma.

This invention contemplates a doubly focusing crystal spectrometer for providing spatially and temporally resolved data on various parameters of an extended hot plasma such as the plasma's ion temperature, plasma rotation, electron temperature, ionization equilibrium, and impurity ion transport. The inventive spectrometer employs a spherically or toroidally curved crystal and takes advantage of the imaging properties of the curved crystal for Bragg angles near 45°. The spherically curved crystal when used at Bragg angles near 45° focuses parallel bundles of X-rays (the cross section of which is determined by the cross section of the crystal) from the plasma to a point on the detector. Parallel rays that are inclined to the main plane of diffraction are focused to different points on the detector. Thus, a spectrally and spatially resolved X-ray image of the plasma is provided on a two-dimensional detector using a single crystal. Obtaining data from all of the different chords through the plasma from the same diffracting element, i.e., the spherically curved crystal, eliminates the necessity for cross-calibration of the data from the different radial chords, thus substantially simplifying the diagnostics system and increasing data throughput. The inventive spectrometer permits radial imaging of the plasma X-ray emission at different wavelengths simultaneously using only a single crystal. Thus, a spectrally and spatially resolved X-ray image of the plasma is provided on a two-dimensional detector using a single crystal.

The inventive X-ray Imaging Crystal Spectrometers can be installed at presently operating devices, such as the Torus Experiment for Technology Oriented Research (TEXTOR) and the National Spherical Torus Experiment (NSTX), to measure the spatial distribution of plasma parameters. Since the spatial resolution in the plasma is determined by the height of the crystal, the X-ray imaging crystal spectrometer employs small spherically or toroidally curved crystals together with a two-dimensionally position-sensitive detector providing spectral information in one direction and spatial information in the other direction. The design of the inventive X-ray imaging crystal spectrometer is therefore distinctly different from the above described design of a doubly focusing spectrometer for future large tokamaks, like ITER, where a large spherically or toroidally curved crystal is needed to enhance the throughput in a (single-chord) instrument (with a one-dimensionally position-sensitive detector) that is far away from the plasma.

The inventive doubly focusing X-ray imaging crystal spectrometer, which employs spherically or toroidally bent crystals, addresses the aforementioned limitations and offers significant advantages over prior experimental arrangements, which include: (1) only one crystal is needed to provide spectra from an essentially unlimited number of lines of sight through the plasma. (2) The spectra from each line of sight are obtained by the entire crystal, so that a cross calibration of spectra from the different lines of sight is not necessary. (3) Compared with Bartiromo's arrangement, which employs a cylindrical crystal, the height of the here proposed spherical crystal is small, since it determines the spatial resolution in the plasma. Contrary to Bartiromo's arrangement, it is not necessary to increase the height of the crystal in order to view a larger section of the plasma, since the observable section of the plasma is independent of the height of the spherical crystal. (4) Due to the additional focusing of the sagittal rays, spherically or toroidally bent crystals provide a significant intensity enhancement over cylindrically bent crystals of the same size.

The inventive doubly focusing X-ray imaging crystal spectrometer is particularly adapted for use with extended hot plasma sources, to provide spatially and temporally resolved data on crucial plasma parameters such as ion temperature, plasma rotation, electron temperature, ioniza- tion equilibrium, and impurity ion transport, but it may also be used in the X-ray spectral analysis of virtually any type of body or object under study.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DETAILED DESCRIPTION OF THE PREFERRED EMBODIMENTS

Figure 1:
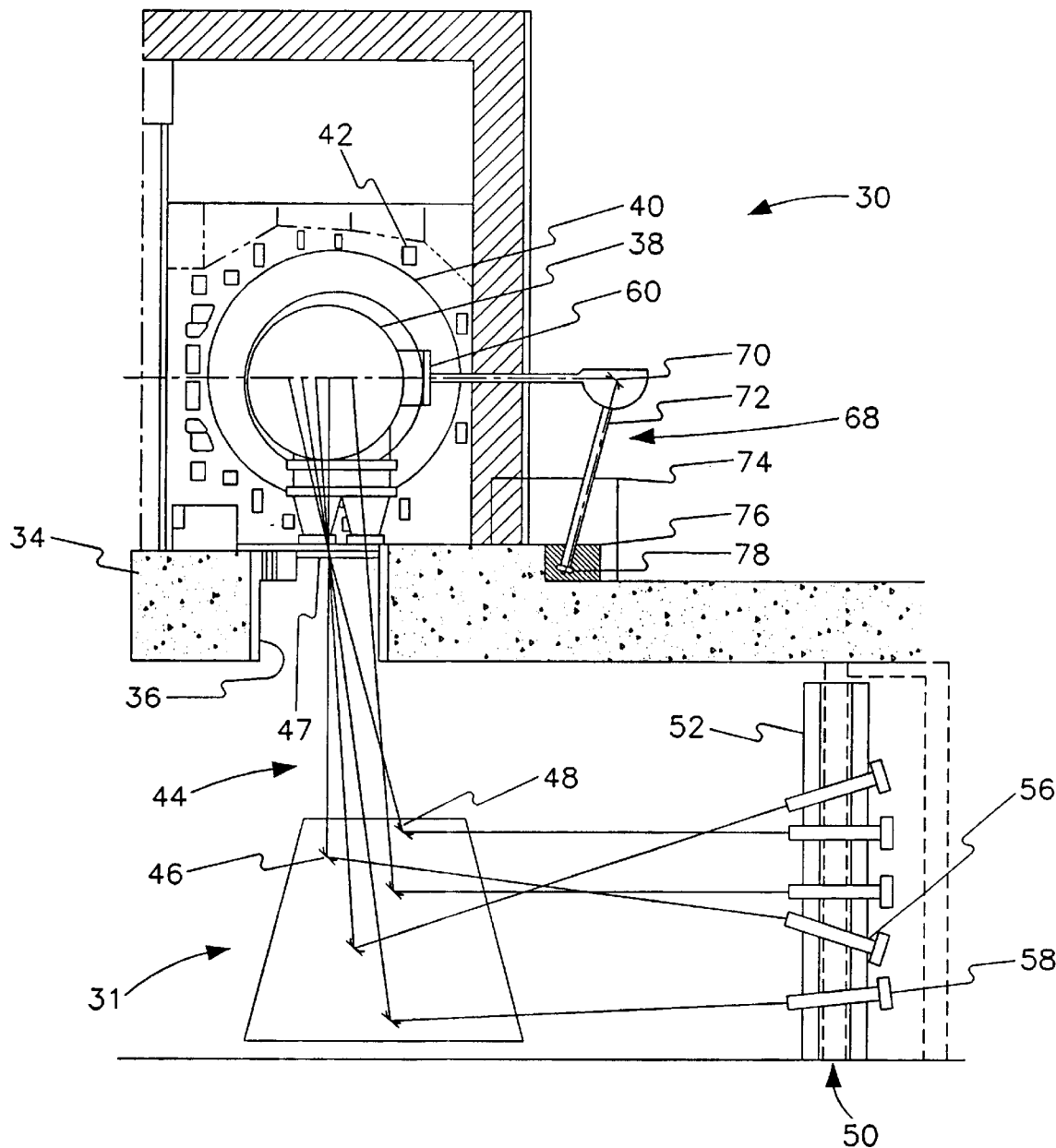
FIG. 1 is a simplified schematic diagram of the vertical X-ray crystal spectrometer array at the Tokamak Fusion Test Reactor incorporating five cylindrically curved crystals illustrating the prior experimental arrangements for measurements of the spatial distribution of plasma parameters.

Referring to FIG. 1, there is shown an array of Johann spectrometers with cylindrically bent crystals illustrating the prior experimental arrangement for measurement of the spatial distribution of plasma parameters in extended plasma sources. FIG. 1 is a simplified schematic diagram of the Tokomak Fusion Test Reactor (TFTR) test cell 30 and test-cell basement incorporating a vertical array of five X-ray crystal spectrometers 31. The TFTR test cell 30 includes a vacuum vessel 38 within which is disposed the hot plasma that emits X-rays 44. The hot plasma is confined by a magnetic field produced by toroidal flux coils 40 and poloidal flux coils 42. The plasma is heated injection of neutral particle beams and ion cyclotron waves in the radio frequency range which are not shown in the figure for simplicity.

The TFTR test cell 30 is disposed on and supported by a floor 34. Floor 34 includes an aperture 36 therein over which is disposed a beryllium window 47. High energy X-radiation from the hot plasma passes through the beryllium window 47 in the form of emitted X-rays 44. The emitted X-rays 44 are reflected by cylindrically curved crystals 46, where five such crystals are shown in the figure. Each of the cylindrically curved crystals 46 is disposed on and supported by a respective crystal mounting structure 48, where five such crystal mounting structures are shown in the figure. The X-rays 44 are reflected by the cylindrically curved crystals 46 onto a detector array 50 inside the shielding structure 52, which consists of lead and borated polyethylene and which provides shielding of the X-ray detector array 50 against the background radiation of neutrons and gammas. A collimator 56 is placed in front of each of the five detectors 58 to reduce the free streaming of neutrons and gammas to the detector. The detectors 58 are multi-wire proportional counters.

A second horizontal X-ray crystal spectrometer 68, also a Johann spectrometer with a cylindrically bent crystal 70, is incorporated in the TFTR test cell 30. This latter spectrometer views the hot plasma through a second beryllium window 60 disposed in the vacuum vessel. The cylindrically curved crystal 70 reflects the emitted X-ray radiation through a helium atmosphere 72 onto a detector 78. Detector 78 is disposed in an array of lead bricks 76 and is further shielded by means of a borated polyethylene shield 74.

It should be understood that the array of the five cylindrically bent crystals, which have been used in the past to obtain spatial resolution of the plasma parameters of TFTR, could be replaced by a single spherically bent crystal, which can simultaneously record spectra from many lines of sight, while in the old TFTR arrangement each of the cylindrically bent crystals only provided a view into the plasma along a single line of sight. The advantage of the new spectrometer design for NSTX, where only one spherically bent crystal is used to accomplish the same task, which previously required an array of crystal spectrometers, is obvious from a comparison of FIGS. 1 and 2.

The two spectrometers in the NSTX rely upon the imaging properties of a spherically curved crystal for Bragg angles near 45° which make it possible to focus a parallel bundle of X-rays emitted from the extended hot plasma onto a point on a detector. The cross section of the bundle of X-rays is determined by the cross section of the spherically curved crystal which reflects the X-rays onto the detector. In one embodiment, the cross section of the spherically curved crystal is on the order of 1 cm×5 cm. Parallel rays of the emitted X-radiation that are inclined to the plane of diffraction are focused onto different points of the detector. Thus, it is possible to radially image the plasma X-ray emission in different wavelengths simultaneously by means of a single crystal. The two spectrometers at NSTX record spectra from lines of sight in the horizontal midplane of NSTX and from lines of sight in a plane perpendicular to the horizontal midplane, respectively. Each of the spectrometers in the NSTX arrangement shown in FIG. 1 includes a respective evacuated (<$10^{-2}$ Torr) crystal-detector arm of about 3 m length. In the arrangement shown in FIG. 1, the first the array 31 of five spectrometers in the TFTR Test Cell Basement views the hot plasma in a vertical plane, while the second X-ray spectrometer 68 views the hot plasma in the horizontal midplane.

Figure 2:
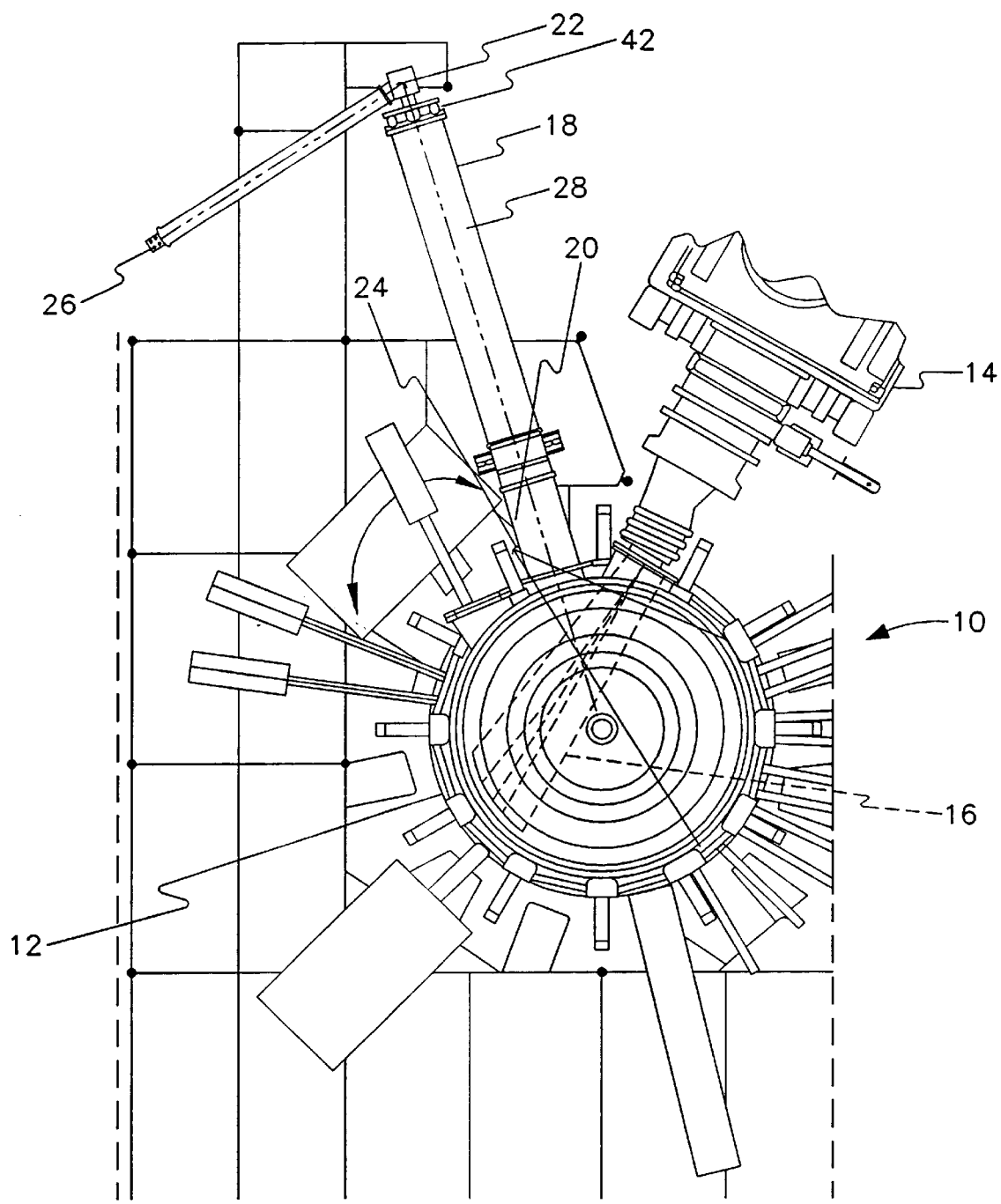
FIG. 2 is a simplified top plan view of an arrangement incorporating two multi-chord X-ray imaging crystal spectrometers in accordance with the present invention for use in the National Spherical Tokomak Experiment.

Referring to FIG. 2, there is shown a top plan view of the National Spherical Tokomak Experiment (NSTX) arrangement 10 incorporating a pair of multi-chord X-ray imaging crystal spectrometers in accordance with the present invention. The NSTX arrangement 10 includes a vessel 12 which is evacuated and contains an extended hot plasma. The hot plasma is in the form of a toroid and is confined by a magnetic field. A neutral-beam source 14 is adjacent to the vessel 12 and directs energetic neutral hydrogen beams 16 into the plasma to heat the plasma. Other forms of energy, e.g. RF waves, may be injected into the plasma for auxiliary heating. Spectral lines emitted by highly ionized ions formed in the hot core of the plasma are obtained by X-ray spectroscopy. Satellite spectra of He-like or H-like impurity ions provide information about the central electron temperature and ion charge-state distribution within the hot plasma. The line widths of resonance lines 1s-2p of such ions yield the ion temperature in the hot core of the plasma. A resolution of $\lambda/\Delta\lambda=10{,}000$, where $\lambda$ is the wavelength of the radiation and $\Delta\lambda$ the change in the wavelength, is necessary for ion temperature measurements.

In accordance with the present invention, the NSTX arrangement 10 includes a first and a second X-ray crystal spectrometer, 18 and 20, for measuring the X-ray radiation emitted by the hot plasma within the vessel. The first X-ray crystal spectrometer 18 includes a first spherically curved crystal 22 and a detector 26 to record spectra from vertical sightlines. An evacuated crystal detector arm 28 is mounted to the vessel 12 and provides access to the plasma within the vessel for the crystal and detector combination via a beryllium window. The second X-ray crystal spectrometer 20 includes a second spherically curved crystal 24 as well as a vertical detector arm, where the detector is located on the floor and is not shown in the figure for simplicity. Each of the spherically curved crystals is on the order of 1 cm×5 cm in size. Spectral and spatial resolution is obtained using the imaging properties of a spherically curved crystal for Bragg angles near 45° and "two dimensional" position sensitive detectors in the form of modified multi-wire proportional counters, X-ray imaging tubes or large flat-panel detectors.

Figure 3:
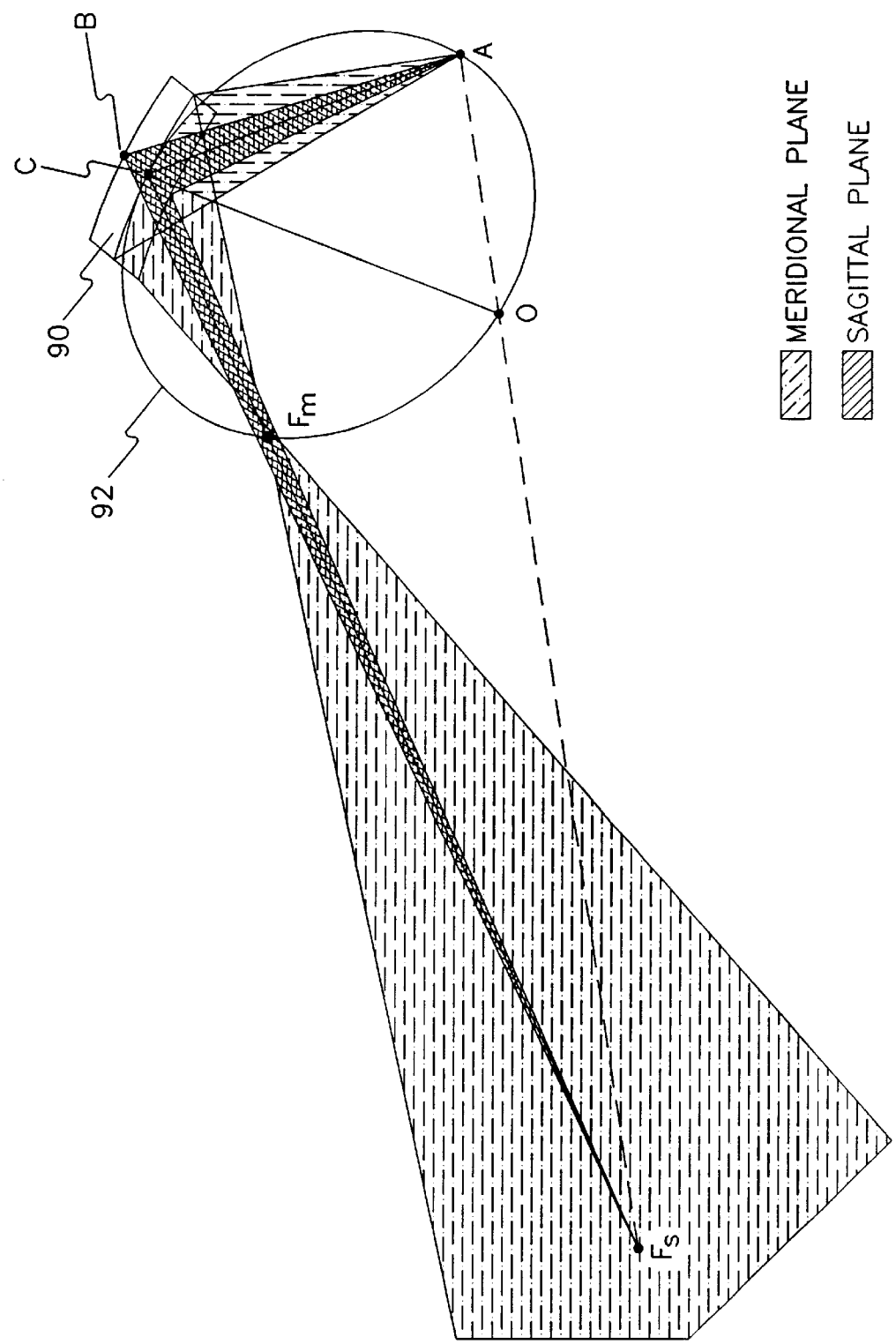
FIG. 3 is an illustration of the focusing properties of a spherically curved crystal for a Bragg angle greater than 45°.

The manner in which the inventive X-ray imaging crystal spectrometer employing a spherically bent reflecting crystal generates a extended field of monochromatic radiation by means of the well-known Bragg reflection method will now be described with reference to FIG. 3, which illustrates the focusing properties of a spherically curved crystal for rays in the meridional (horizontal) plane and the central sagittal (vertical) plane. Extended fields of monochromatic, near parallel radiation are of interest for many applications, including lithography and medical applications. An X-ray point source, e.g. the small (point-like) exit aperture of an X-ray tube, and a spherically bent crystal are aligned with reference to a circle 92, called the Rowland circle, having one-half the radius of curvature of the spectrometer's spherically bent reflecting crystal 90. The center of the crystal touches the Rowland circle in point C. The center of the crystal's sphere is at point O. $F_m$ and $F_s$ are the focal points in the meridional plane and the central sagittal plane, respectively, which intersects the crystal in line CB. Rays, which emanate from a point-source at A and which fulfill the Bragg condition, are reflected from the crystal and focused at points, like Fm and Fs, which represent focal points for the meridional and sagittal rays, respectively. The Bragg condition requires that the wavelength X of the reflected radiation is given by $$\lambda = 2d \sin(\Theta) \qquad (1)$$

where d is the spacing of the reflecting lattice planea of the crystal and $\Theta$ the Bragg angle, i.e. the angle between the incident ray and a tangent to the lattice plane, which is usually parallel to the surface of the crystal. The location of the focal points Fm and Fs for the meridional and sagittal rays also depends on the Bragg angle $\Theta$. The ratio of the focal lengths fm and fs, which correspond to the distances of $F_m$ and $F_s$ from the center of the crystal, is given by $$F_s/F_m = -1/\cos(2\Theta)) \qquad (2)$$

A X-ray tube emits in addition to the line radiation, which is characteristic for the material of the target of the X-ray tube, bremsstrahlung radiation with a continuous or white energy spectrum. If such a X-ray point source is placed at a point on the Rowland circle, e.g. the point A in FIG, 3, the Bragg condition will be fulfilled for X-rays of a certain energy or wavelength, $\lambda$. Only X-rays of this particular wavelength $\lambda$ will be reflected from the crystal and form an extended field of monochromatic radiation as shown in FIG. 3. The lateral dimensions of the radiation field are determined by the size of the crystal. The Bragg angle $\Theta$ and thus the wavelength $\lambda$ of the radiation field can be selected or tuned by moving the point source on the Rowland circle. It should be understood that the X-ray tracing in the here described application, namely, the generation of an extended field of monochromatic radiation, is reversed from the X-ray tracing, which is normally used, when the spectrometer is employed for the diagnostics of an extended plasma source. In the latter case, a detector is placed at point A to record the radiation emitted from an extended plasma source. The radiation emitted from the plasma passes through $F_m$ and $F_s$, is reflected from the crystal and focused onto the detector at point A.

Equation (2) has important consequences for the design of a crystal spectrometer for the diagnostics of extended plasma sources. Using equation (2), the dimensions of the projected cross section of the spherical crystal at the center of the plasma can be calculated. For near parallel collimation of the sagittal rays, which can be obtained for Bragg angles near 45°, the X-rays can be transmitted through a window in the vacuum vessel of essentially the same diameter as that of the spherically curved crystal. This is a substantial advantage, if the spectrometer is used at future large tokamaks, like ITER, where the diagnostic windows on the vacuum vessel must be kept as small as possible and where the distance between the plasma and the spectrometer must be large, because of operating constraints. In fact, at ITER the distance between the plasma and the crystal will be about 20 m or even larger. Under these conditions, the throughput obtained with large, spherically or toroidally curved, crystals will be about 20 times the throughout of the currently used cylindrically curved crystals. The present inventors have shown theoretically and experimentally that crystals as large as 33 cm×33 cm in size may be used with spherical or toroidal curvature.

However, Bragg angles near 45° are also of interest for the diagnostics of the extended plasma sources of present-day tokamaks, where the experimental constraints are less restrictive, so that it is possible to view a large section of the plasma and to measure the spatial distribution of plasma parameters by means of an imaging X-ray crystal spectrometer, which has been described above. By recording the spectra with near parallel rays the Abel inversion of the raw data is greatly simplified.

With reference to the schematic diagram shown in FIG. 5, the manner in which a reflecting crystal may be accurately bent to a desired curvature for use in the invented X-ray spectrometer will now be described. An optically accurate glass mirror 94 having a spherical or toroidal surface is provided with a small aperture 95 drilled through its center. A crystal disc 96, e.g. a silicon wafer, is held by means of the spherical or toroidal glass mirror 94 and the volume between the Si disc and the mirror surface is evacuated through the small aperture 95 in the glass mirror 94 by means of a vacuum source 97. The crystal disc 96 then assumes the curvature of the glass mirror 94. The size of the crystal is determined, in the case of Si, by the diameter of the ingot which may reach 12" for the (4,0,0) reflection, using the cut employed in the solid state industry. However, the ingot could be cut perpendicular to the (1,0,0) direction, such that the surface is parallel to the (2,2,0) direction which has the best X-ray reflection properties for the diamond lattice. There is essentially no limit to the length of such a crystal. The availability of such large crystals is especially important for the generation of an extended field of monochromatic radiation, which is one aspect of this invention.

The Johann error is an inherent focusing error of the Johann spectrometer. This focusing error affects the spectral resolution; it increases with the size of the crystal and decreases with increasing Bragg angle. It is therefore possible to obtain a fixed value of the spectral resolution of, e.g. 10000, for a variety of Bragg angles and crystal sizes. At 70°, the width of a crystal with a radius of curvature of 10 m may reach 76 cm and the instrumental width due to the Johann error can be 2.6 mm still providing a spectral resolution of 10,000. With this size of reflecting crystal, it has been found that the diagnostic throughput increased by an order of magnitude for the two-dimensional spherically or toroidally curved crystal spectrometer over the prior art of cylindrically curved crystal spectrometer for Bragg angles above 50°.

The throughput of large two-dimensional spherically curved crystal X-ray spectrometers in accordance with the present invention with a reflecting crystal having 10 m radius of curvature was found by ray-tracing to be larger by more than an order of magnitude than that of the currently used cylindrically curved crystal spectrometers for Bragg angles greater than 50°. The results of ray-tracing were confirmed by experiment.

The experiment was performed with a Si wafer disc of 200 mm diameter and 0.625 mm thickness, which had been spherically bent to a radius of curvature of 6.35 m by the method described above. The crystal was illuminated by an X-ray point source (the 'point-like' aperture of an X-ray tube) which was positioned on the Rowland circle, such that the Bragg angle for the rays incident on the crystal was 75°. The reflected, monochromatic radiation is focused on a line segment perpendicular to the plane of the Rowland circle 92 and to a line segment in the plane of the Rowland circle, as shown in FIG. 3. These line segments represent the foci for the meridional and sagittal rays, respectively. The second focus may be used to obtain the spatial distribution of the impurity ions in the plasma, in a direction perpendicular to the plane of the Rowland circle.

A toroidally curved crystal focuses the monochromatic radiation perfectly, if the radii of curvature of the toroidal surface are chosen such that the focal points $F_m$ and $F_s$ coincide. A point of a line source, which is perpendicular to the plane of the Rowland circle and intersects the Rowland circle, will then be focused to a point. Thus, the intensity distribution along a spectral line will yield the density distribution of the ion involved. Moreover, variations of the line width along the line will yield the ion temperature distribution in the plasma. This measurement can be made for a small wavelength range only, since $F_m$ and $F_s$ will be coincident only for one Bragg angle. Ray-tracing calculations have shown that the images of a point source provided by a toroidal crystal, for the aforementioned parameters of the spectrometer, are of minute dimensions. For a Bragg angle $\Theta=60°$, the largest diameter of the image of a point source, the so-called spot-size, is 0.1 micron, 0.1 mm, and 0.5 mm, if the point source is 0, 2 and 4 cm above the plane of the Rowland circle, respectively. The spatial resolution will change only slowly over the small wavelength range covering He-like and Li-like spectra of highly ionized ions of a given element.

Figures 4, 5:
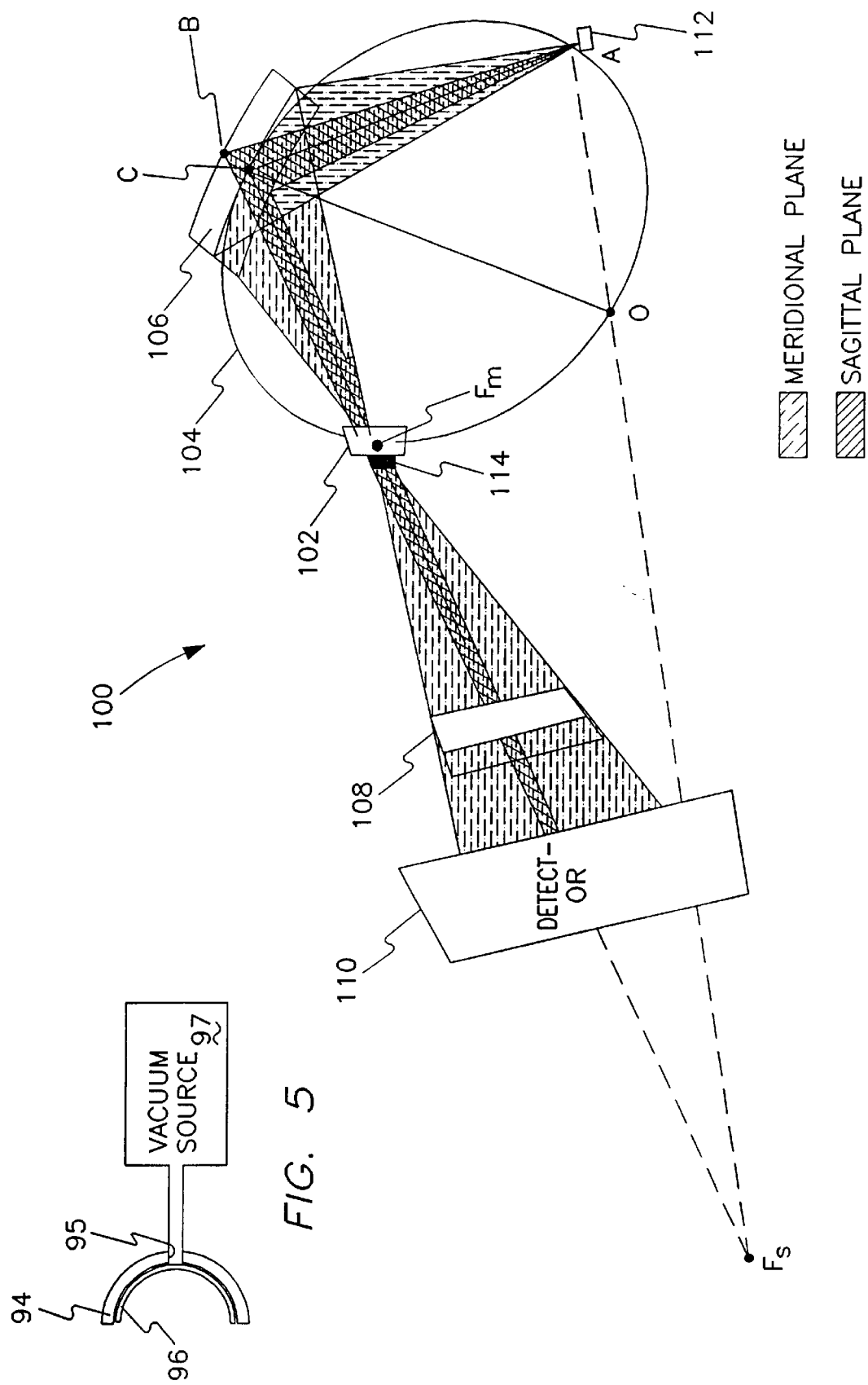
FIG. 4 is a simplified schematic diagram illustrating the use of an X-ray spectrometer in accordance with the present invention in the spectral analysis of an object under study.
FIG. 5 is a simplified schematic diagram of an arrangement for forming two dimensionally curved reflecting crystals used in the present invention.

Referring to FIG. 4, there is shown a simplified schematic diagram of a curved crystal X-ray spectrometer 100 for spectrally analyzing the composition of virtually any type of object or body. As in FIG. 3, FIG. 4 shows a Rowland circle 104 which defines the spatial relationships of various components of the X-ray spectrometer 100. For example, at point A is located a X-ray source 112, such as a high intensity X-ray tube, for directing X-rays onto a spherically or toroidally curved crystal 106. As in the previously described embodiment, both point A (X-ray source 112) and the curved crystal 106 are disposed on the Rowland circle 104. In this embodiment of the invention, using a large spherically curved crystal 106 in combination with a source 112 comprised of a high intensity X-ray tube having a 0.1 mm wide slit disposed at point A on the Rowland circle 104, it is possible to produce an extended monochromatic and homogeneous radiation field of nearly parallel rays using a Bragg angle near 45°. In this situation, the reflected sagittal rays are parallel. If the Bragg angle is larger than 45°, the reflected sagittal rays are convergent. The meridional rays are focused at the points Fm which fall on a line segment perpendicular to the plane of the Rowland circle. Along this line segment, the radiation is very intense due to the focusing of the meridional rays. The length of this line segment is determined by the height of the crystal. In general, the cross section of the radiation field is everywhere determined by the size of the curved crystal. In one experimental arrangement, an object 102 undergoing spectroscopic analysis can be placed at the location of the line segment formed by the points Fm, and a detector 114, which is position-sensitive in a direction parallel to this line segment, can be placed behind the object to measure the transmitted radiation. The object 102 can be displaced to allow the X-rays to scan over the entire object. The here described use of the X-ray spectrometer 100 as an X-ray monochromator and the particular arrangement of object and detector, which allows for the scanning of an object through an intense line source, would have wide application in various fields such as in the spectroscopic analysis of paintings, medical imaging, etc. It should be noted that in this arrangement the object 102 is placed on the Rowland circle 104.

FIG. 4 shows another embodiment of the curved crystal X-ray spectrometer 100 which does not require scanning of the object under analysis by the incident X-ray beam. In this embodiment, the object 108 (shown in dotted line form) under analysis is disposed at a location where the radiation field has a large cross section. This is the case at locations inside and outside of the Rowland circle 104. A detector 110 (also shown in dotted line form) is disposed behind the object 108 also in the path of the diverging X-ray beam for receiving the X-rays which pass through the object. In this latter arrangement, it is not required to scan the X-ray beam over the object 108 because the detector 110 is large enough to receive all of the radiation passing through the object. The detector should be a two-dimensional position-sensitive detector, as, for instance, a X-ray imaging tube or one of the new large, flat-panel detector, which are already in use for medical imaging.

There has thus been shown a high-resolution X-ray imaging crystal spectrometer which is particularly adapted for (1) the diagnostics of extended X-ray sources, such as hot plasmas produced in thermo-nuclear fusion experiments and (2) the generation of extended fields of monochromatic X-ray radiation, which fields may have wide spread applications in lithography, medicine and, in general, the spectroscopic investigation of objects. The spectrometer employs a spherically or toroidally curved crystal for reflecting the X-rays onto a detector. The imaging properties of the spherically or toroidally curved crystal provide both spectrally and spatially resolved X-ray data from extended plasma sources. The spectrometer can be adapted to the experimental requirements of both future large fusion devices, such as ITER, and the diagnostic needs of present-day tokamaks and stellarators. The demands are distinctly different. In the first case, the spectrometer will operate with a very large spherically or toroidally curved crystal to enhance the instrumental throughput, using near parallel X-ray radiation at Bragg angles of 45°, to cope with the experimental constraints of small diagnostic windows and large distances between spectrometer and plasma. In the second case, where the access to the plasma is less restrictive, the spectrometer will operate as an Imaging X-ray Crystal Spectrometer, which provides information on the spatial distribution of plasma parameters. Such an Imaging X-ray Crystal Spectrometer will use only a small spherically or toroidally curved crystal, thus eliminating the requirement for a large array of crystal spectrometers and the need to cross-calibrate the various crystals. For Bragg angles near 45°, the curved crystal focuses a bundle of X-rays (the cross section of which is determined by the cross section of the crystal) from the plasma to a point on a detector, with parallel rays inclined to the main plane of the diffraction focused to different points on the detector. This makes it possible to radially image the plasma X-ray emission in different wavelengths simultaneously with a single crystal in providing spatially and temporally resolved data on the aforementioned plasma parameters. The spatial resolution in the plasma is determined by the height of the crystal, which has therefore to be small. The use of near parallel radiation at Bragg angles of 45° facilitates the Abel inversion of the raw data.

X-ray measurements of plasma parameters, such as ion temperature, toroidal and poloidal rotation, electron temperature, impurity ion charged-state distributions, and impurity transport, require crystal spectrometers with high spectral and spatial resolution. The aforementioned parameters are usually determined from the line spectra of heliumlike ions, such as ArXVII, CrXXIII, FeXXV, which exist in hot plasmas for a wide range of electron temperatures. Impurities are introduced to the plasma either as indigenous impurities from the wall or the vacuum vessel of by injection for diagnostic purposes. For diagnostic purposes, it is important to select the appropriate impurity in accordance with the parameters of an experiment. Helium-like argon, ArXVII, is the dominant charge state for electron temperatures in the range of 0.4–3.0 keV that is accessible in such plasma fusion experiments as the NSTX. It has been demonstrated in experiments at TEXTOR that a throughput of 2×105 photons/s, corresponding to the count rate limit of employed detector, can easily be obtained with small, non-perturbing argon gas puffs of less than 1×10−3 Torr liter/sec, so that it is possible to record spectra with a small statistical error and good time resolution (typically 50 m sec, and 1 msec in some cases). Employing spherical crystals, the inventive spectrometer provides spectrally resolved images of the plasma for all experimental conditions, which include ohmically heated discharges as well as plasmas with RF and neutral-beam heating. The inventive spherically or toroidally curved crystal spectrometer may also be used for the spectral analysis of the composition of virtually any type of object or body under study.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawing is offered by way of illustration only and not as a limitation. The actual scope of the invention is intended to be defined in the following claims when viewed in their proper perspective based on the prior art.

We claim:

1. An imaging spectrometer for spectral analysis of an extended hot plasma emitting X-rays, said spectrometer comprising:

an X-ray detector;

an elongated evacuated tube connected to an access window in a closed reactor vessel containing hot plasma for directing X-rays emitted by the hot plasma to a two dimensionally curved crystal; and the two dimensionally curved crystal for reflecting X-rays emitted by the hot plasma onto said X-ray detector, wherein said crystal has a main radius of curvature $R_1$ and said curved crystal and said X-ray detector are disposed on a common circle having a radius $R_2$, where $R_1$ and $R_2$ are chosen so as to position focal lines for the meridional and sagittal rays according to localized measurements of the X-ray emissivity and the plasma parameters of the extended hot plasma and wherein the hot plasma, said X-ray detector and said curved crystal define a main diffraction plane, wherein said curved crystal reflects X-rays emitted by the hot plasma onto said X-ray detector at a Bragg angle of, or approximately equal to 45°, so that said curved crystal focuses X-rays which are near-parallel to said main diffraction plane to a central point on said X-ray detector and focuses near-parallel X-rays inclined to said main diffraction plane to different spaced points on said X-ray detector.

2. The spectrometer of claim 1 wherein said crystal is spherically curved.

3. The spectrometer of claim 1 wherein said crystal is toroidally curved having a first radius of curvature in a first plane through said crystal and a second radius of curvature through a second plane through said crystal, wherein said first and second planes are orthogonal.

4. The spectrometer of claim 1 further comprising means for maintaining said crystal in a two dimensionally curved configuration.

5. The spectrometer of claim 4 wherein said means for maintaining said crystal in a curved configuration includes a two dimensionally curved rigid support member attached to said crystal and means for drawing said crystal into close-fitting engagement with said curved support member.

6. The spectrometer of claim 5 wherein said means for drawing said crystal into close-fitting engagement with said curved support member includes a vacuum source.

7. The spectrometer of claim 1 wherein said common circle is a Rowland circle.

8. An X-ray spectrometer for analyzing the composition of an object, said spectrometer comprising:

a small source of X-rays;

a detector responsive to X-rays incident thereon; and a two dimensionally curved crystal for reflecting X-rays from said source at a Bragg angle of, or approximately equal to 45° and providing an extended field of monochromatic radiation with two orthogonal focal lines, wherein said radiation field penetrates the object providing an X-ray image of the object onto said detector, wherein said crystal has a radius of curvature $R_1$ and said crystal and said source of X-rays are disposed on a common circle having a radius $R_2$, where $R_1 = 2R_2$.

9. The spectrometer of claim 8 wherein the object and said detector are also disposed on said common circle and said common circle is a Rowland circle.

10. The spectrometer of claim 8 wherein said crystal is spherically curved.

11. The spectrometer of claim 8 wherein said crystal is toroidally curved having a first radius of curvature in a first plane through said crystal and a second radius of curvature through a second plane through said crystal, and wherein said first and second planes are orthogonal, and wherein the second radius of curvature of the crystal is chosen so as to provide an extended radiation field.

12. The spectrometer of claim 8 wherein said crystal is comprised of silicon, germanium, or any crystal having a large size and capable of providing a radiation field having a large cross-section.

13. The spectrometer of claim 8 further comprising means for maintaining said crystal in a curved configuration.

14. The spectrometer of claim 13 wherein said means for maintaining said crystal in a curved configuration includes a two dimensionally curved rigid support member attached to said crystal and means for drawing said crystal into close-fitting engagement with said curved support member.

15. The spectrometer of claim 14 wherein said means for drawing said crystal into close-fitting engagement with said curved support member includes a vacuum source.

* * * * *